United States Patent [19]
Crockard et al.

[11] Patent Number: 5,879,385
[45] Date of Patent: Mar. 9, 1999

[54] SURGICAL IMPLANT

[75] Inventors: Hugh Alan Crockard, Highgate, United Kingdom; Raphael Meloul, Atlanta, Ga.; Ronald A. Yapp, Phoenix, Ariz.

[73] Assignee: Hillway Surgical Limited, Highgate, United Kingdom

[21] Appl. No.: 259,328

[22] Filed: Jun. 13, 1994

Related U.S. Application Data

[63] Continuation-in-part of Ser. No. 75,733, Jun. 11, 1993, abandoned.

[51] Int. Cl.⁶ .................................................. A61F 2/44
[52] U.S. Cl. ............................................... 623/17; 606/61
[58] Field of Search ........................... 623/16, 17; 606/61, 606/74, 69

[56] References Cited

U.S. PATENT DOCUMENTS

| | | |
|---|---|---|
| 3,648,691 | 3/1972 | Lumb . |
| 3,693,616 | 9/1972 | Roaf et al. ................................ 606/69 |
| 3,741,205 | 6/1973 | Markolf . |
| 4,604,995 | 8/1986 | Stephens . |
| 4,686,970 | 8/1987 | Dove et al. ............................... 606/61 |
| 4,836,193 | 6/1989 | Ransford .................................. 606/61 |
| 5,133,716 | 7/1992 | Plaza ........................................ 606/61 |
| 5,573,454 | 11/1996 | Hoffman . |

FOREIGN PATENT DOCUMENTS

| | | |
|---|---|---|
| 0146347 | 12/1984 | European Pat. Off. . |
| 2 656 214 | 6/1991 | France . |
| 1551704 | 10/1975 | United Kingdom . |
| 1538080 | 10/1976 | United Kingdom . |
| 2151928B | 12/1984 | United Kingdom . |
| 89 08431 | 9/1989 | WIPO . |
| 90 04366 | 5/1990 | WIPO . |
| 9004948 | 5/1990 | WIPO ...................................... 606/61 |

OTHER PUBLICATIONS

Lea Plaxa C et al, "Surgical Correction of Scoliosis with a New Three–Dimensional Device, the Lea Plaza Frame"SPINE, vol. 17, No. 3, 1992, pp. 365 to 372.

Herring J.A., et al, "Segmental Spinal Instrumentation—a Preliminary Report of 40 Consectuive Cases", SPINE, vol. 7, No. 3, 1982, pp. 285 to 298.

Luque E.R. et al, "Segmental Spinal Instrumentation in Treatment of Fractures of the Thoracolumbar Spine", SPINE, vol. 7, No. 3, 1982, pp. 312 to 317.

Seifert V. et al, "Cranio–Cervical Stabilization Using Contoured Luque Rectangles", ACTA Neurochirurgica (Vienna), (1991) 109: 20–25.

Mackenzie A.I. et al, "Craniocervical Stabilization Using Luque/Hartshill Rectangles", Neurosurgery, vol. 26, No. 1, pp. 32 to 36.

Luque E.R. "The Anatomic Basis and Development of Segmental Spinal Instrumentation", SPINE, vol. 7, No. 3, 1982, pp. 256 to 259.

*Primary Examiner*—John G. Weiss
*Attorney, Agent, or Firm*—Wolf, Greenfield & Sacks, P.C.

[57] ABSTRACT

A surgical implant for spinal fixation formed by a rigid bent titanium frame having wire receiving means. Spinal fixation implants are used to correct abnormal curvature of, and/or impart stability to, the spine by immobilising a plurality of vertebrae with respect to each other. A rigid bullet shaped frame which fits neatly onto the posterior surface of the spine to embrace at least two bones is fixed in place by means of fixation wires passed around or looped through the frame and passing through holes in the bones to immobilise the embraced bones with respect to each other. The frame has a substantially rectangular cross-section. An improved surgical implant results from the provision of wire receiving means which prevent the fixation wires moving relative to the frame and the bullet shaped frame of rectangular cross-section which improves the stability of a fixed implant by close conformity of the implant to the shape of the spine.

16 Claims, 7 Drawing Sheets

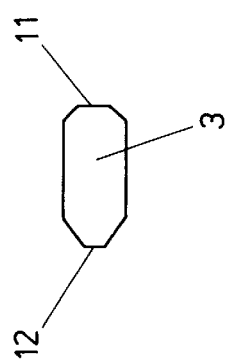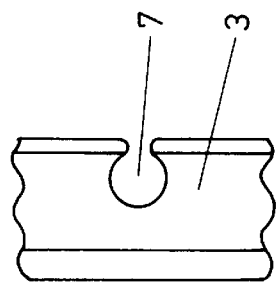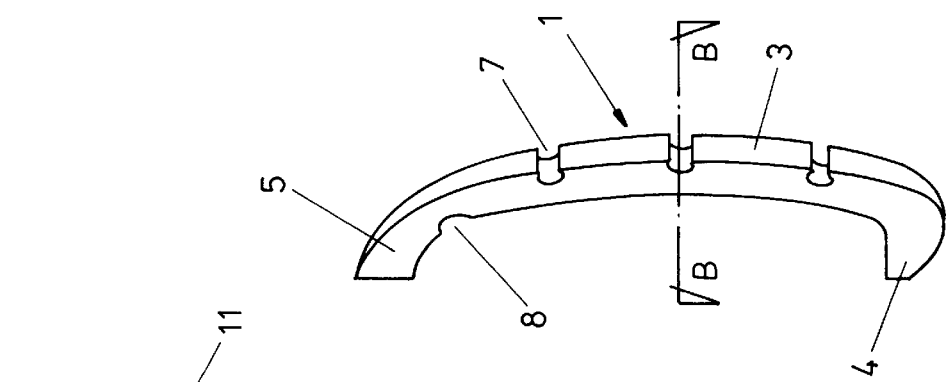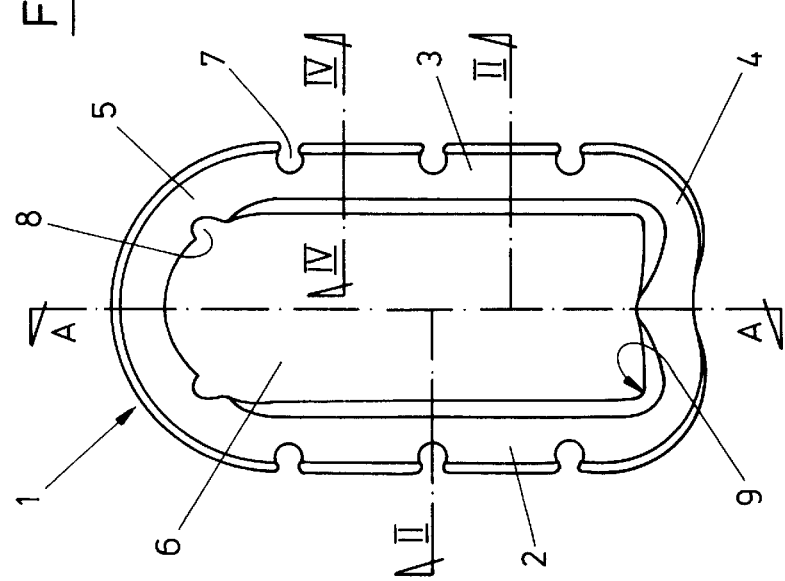

SURGICAL IMPLANT

RELATED APPLICATION

This is a continuation-in-part of application Ser. No. 08/075,733 filed Jun. 11, 1993, abandoned.

FIELD OF THE INVENTION

Background of the Invention

This invention relates to surgical implants for spinal fixation.

Spinal fixation implants are used to correct abnormal curvature of, and/or impart stability to, the spine by immobilising a plurality of vertebrae with respect to each other. A rigid frame which fits neatly onto the posterior surface of the spine to embrace at least two adjacent vertebrae is fixed in place by means of fixation wires (or cables) passed around or looped through the frame and passed under the laminae to immobilise the embraced vertebrae with respect to each other.

One type of known spinal fixation implant comprises stainless steel or titanium rods formed into a rectangle. The fixation wires are looped around the rod to secure the rectangle to the spine. A problem with such implants is that any tensile or compressive forces parallel to the direction of the spine will cause the implant to slip relative to the fixation wires as soon as the frictional force between the wire and rod is overcome. A further problem of prior art implants is the dead space between a fitted implant and the spine arising from a lack of conformity between the contours of the cervical spine and the spinal implant.

SUMMARY OF THE INVENTION

According to the invention in a first aspect, there is provided a surgical implant for spinal fixation comprising a rigid biocompatible frame defining an aperture, the frame consisting of first and second substantially parallel frame portions connected by third and fourth frame portions extending in the same direction as each other away from a plane defined by the first and second frame portions, and at least one of the third and fourth frame portions being curved so as to define a tapered portion of relatively small width which, in use, can be fitted closely about the spine. In a preferred form, the frame defines a bullet-shaped aperture, that is, three sides of the frame, when viewed from above, define a substantially rectangular space which is extended at one end towards a point defined by either straight or curving converging frame portions.

The present invention also provides a surgical implant for spinal fixation comprising a rigid biocompatible frame defining an aperture, the frame consisting of first and second substantially parallel frame portions connected by third and fourth frame portions, the third and fourth frame portions extending in the same direction as each other away from the plane defined by the first and second frame portions, the frame having wire receiving means for receiving wire (or cable) at at least one point on the frame and fixed relative thereto, the wire receiving means being a recess formed in one of the frame portions.

Preferably the frame is formed from titanium alloy (Ti-6Al-4V) sheet stock and has flat surfaces.

Embodiments of the present invention will now be described, by way of example, and with reference to the accompanying drawings, in which:

BRIEF DESCRIPTION OF THE DRAWINGS

FIG. 1 is a plan view of a surgical implant embodying the present invention;

FIG. 2 is a section along line II—II of FIG. 1;

FIG. 3 is a side view of the implant of FIG. 1;

FIG. 4 is a section along line IV—IV of FIG. 1;

FIG. 5 illustrates one of the slots in the implant of FIG. 1;

DETAILED DESCRIPTION

Figure 7:
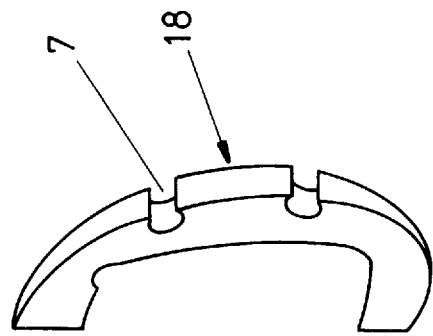
FIGS. 6 and 7 are plan and side views respectively of an alternative embodiment of the present invention.

Referring to FIGS. 1 to 3, a titanium alloy frame 1 having first and second substantially parallel frame portions 2,3 respectively, connected by first and second bent shorter end frame portions 4,5 respectively, defines an aperture 6 for receiving projecting spinal elements. The frame 1 has slots 7 and grooves 8 for receiving fixation wires or cables.

The frame 1 is formed from titanium alloy (Ti-6Al-4V) sheet stock. The frame portions 2,3,4,5 are each approximately 0.35 inches (0.9 cm) wide and 0.125 inches (0.4 cm) thick. All the frame edges are either chamfered or rounded (see FIG. 4). Referring to FIG. 1, the first frame end portion 4 curves slightly into the aperture 6 defining wire seats 9, and the second frame end portion 5 is semi-circular. The frame 1 is approximately 2.35 inches (6 cm) in length from the top of the second end portion 5 to the bottom of the first end portion 4 with the second end portion 5 being defined by a circle of approximately 0.72 inches (1.83 cm) radius. The aperture 6 is approximately 0.8 inches (2 cm) wide.

The parallel frame portions 2, 3 each have three slots 7 in the frame edge 11 remote from the aperture 6. The slots 7 are spaced approximately 0.55 inches (1.4 cm) apart on each parallel frame portion 2,3 with the slots closest to the second end portion 5 being approximately 0.72 inches (1.83 cm) from the top of the second end portion 5. Referring to FIG. 5, each slot 7 has its centre line substantially orthogonal to the frame edge 11 remote from the frame aperture 6 and is defined by an opening 16 0.08 inches (0.2cm) wide in the frame edge 11 which communicates with a cylindrical hole 17 0.055 (0.14 cm) inches in radius having its centre 0.065 inches (0.165 cm) from the frame edge 11.

The second end portion 5 has two grooves of semi-circular section in the frame edge 12 adjacent to the frame aperture 6. Each groove 8 is defined by a circle approximately 0.055 inches (0.14 cm) in radius having its centre on the frame edge 12 adjacent the frame aperture 6 approximately 0.41 inches (1.04 cm) below the top of the second end portion 5.

The middle section 10 of each of the end portions 4,5 bends through an angle of approximately 100° (preferably 102°) as shown in FIG. 2, and the parallel frame portions 2,3 of the frame 1 curve as shown in FIG. 3 so as to accomodate lordosis (or kyphosis) in the spine. The lordotic curve of frame 1 is defined by an arc of a circle, the radius of the circle being in the range 5 to 7 inches (13.2 to 17.8 cm). Preferably, the frame 1 of length 2.35 inches (6 cm) is available in three different lordotic curvatures: flat, arc of a circle of 5 inches (13.2 cm) radius and arc of a circle of 7 inches (17.8 cm) radius.

In use, the titanium alloy frame 1 is placed over the spinous processes on the lamina with the substantially parallel frame portions 2,3 lying substantially parallel to the spine axis with vertebrae elements (the spinous processes) being received in the frame aperture 6. The vertebrae received within the frame 1 are immobilised with respect to each other and the frame 1 by fixation wires or cables looped around the frame 1 and around the lamina of adjacent vertebrae. Fixation wires or cables are looped through the slots 7, the grooves 8 and wire seats 9.

The prior art spinal implants are smooth rectangular frames formed from metal rods. Whereas in the prior art spinal implants the looped fixation wires or cables are prone to slip parallel to the frame portion around which they are looped, in the frame 1 of the present invention the fixation wires or cables are secured within a slot 7 or groove 8 and can therefore resist forces parallel to the frame portion around which they are looped. The frame 1 of the present invention can therefore be rigidly anchored to the spine.

As will be seen from the drawings, the preferred form of frame is symmetrical about a central plane along the longitudinal axis of the device (A—A in FIG. 3), having long portions (2,3) which are substantially parallel (when viewed from above) to the longitudinal axis A—A, and interconnecting portions at either end. The interconnecting portions at each end are asymmetrical about an axis B—B, see FIG. 3; one a continuous tapering arc connecting the long sides (2,3) to define a converging region of somewhat 'pointed' shape, and the other a substantially straight portion at approximately ninety degrees to the long portions. As a whole, when viewed as in FIG. 1, the frame defines an aperture similar in shape to a bullet. When viewed from the side, see FIG. 3, the long sides of the loop formed by the frame are coplanar and shaped to form a curve which roughly approximates the curve of the spine. In end view, FIG. 2, the interconnecting portions (4,5) extend out of the plane of the long sides, defining a rise at either end, having its apex in the plane A—A shown in FIG. 1.

The bullet shaped implant 1 of rectangular cross-section has superior conformance, at the upper and lower ends of the cervical spine, to the contours of the cervical spine in comparison to the prior art rod cross-sectional rectangular frames. The bullet shaped frame 1 can be used pointing to the head in the lower cervical spine, while at the craniovertebral junction, its reversal, to allow the substantially straight end frame portion 4 to nestle against the occiput provides an excellent fixation for the craniovertebral junction. The slots 7 on the frame 1 about every 1.5 cm are compatible with Titanium cable and, by fixing sublaminar cables through the slots 7 provide an extremely firm fixation far in excess to that provided by the conventional prior art rectangular frame arrangement.

Figure 6:
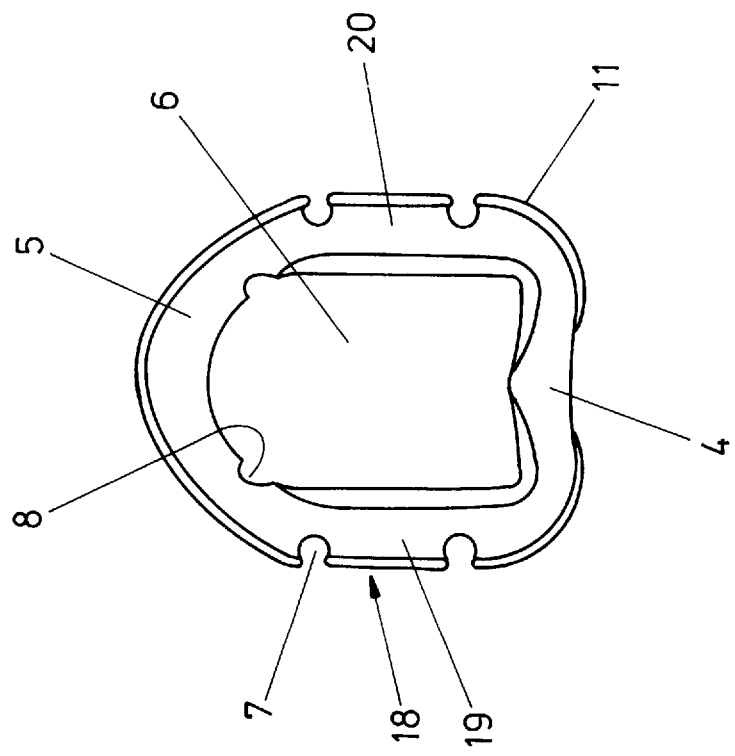

FIGS. 6 and 7 illustrate a titanium frame 18 similar to that of FIGS. 1 to 4 but having substantially parallel frame portions 19,20 of different dimensions. The frame 18 is approximately 1.57 inches (4 cm) in length from the top of the second end portion 5 to the bottom of the first end portion 4. The substantially parallel frame portions 19,20 each have two slots 7 in the frame edge 11 remote from the frame aperture 6, with the slots 7 being spaced approximately 0.55 inches (1.4 cm) apart and the slot closest to the second end portion 5 being approximately 0.6 inches (1.5 cm) from the top of the second end portion 5. Preferably, the frame 18 of FIGS. 6 and 7 is available in three different lordotic curvatures; flat, arc of a circle of 4 inches (10.2 cm) radius and arc of a circle of 7 inches (17.8 cm) radius.

Figure 9:
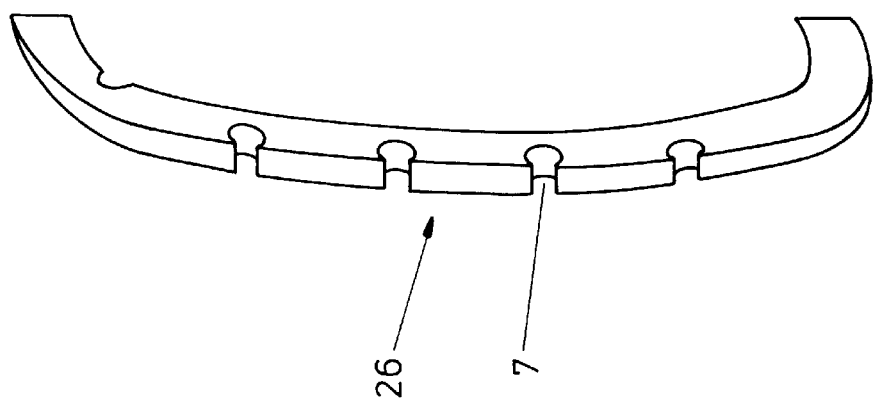
FIGS. 8 and 9 are plan and side views respectively of a further alternative embodiment of the present invention.
Figure 8:
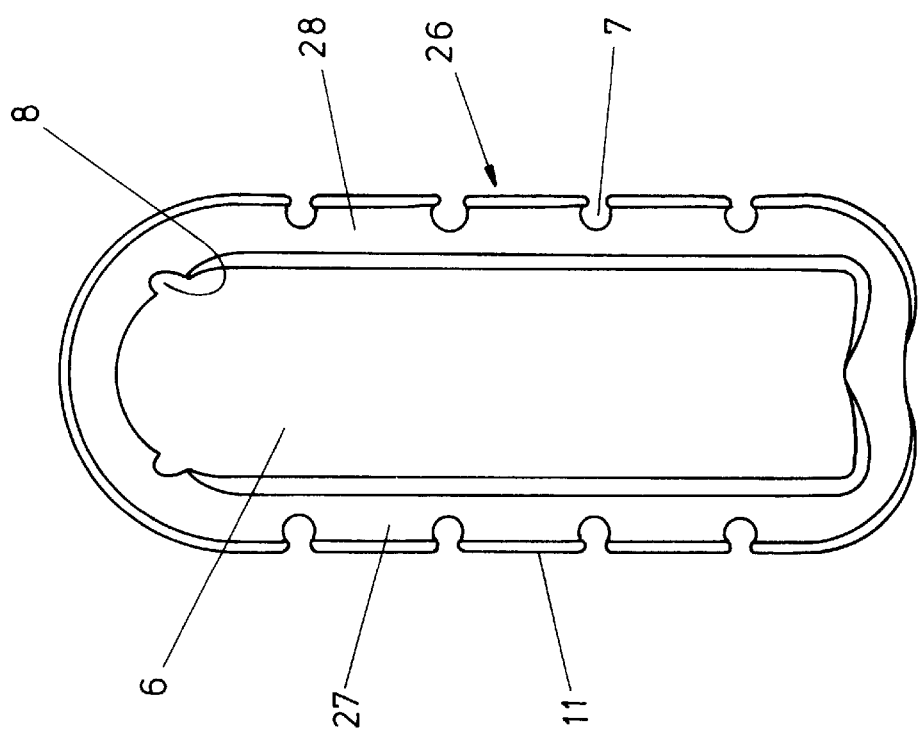

FIGS. 8 and 9 illustrate a titanium frame 26 similar to those of FIGS. 1 to 7 but having substantially parallel frame portions 27,28 of different dimensions. The frame 26 is approximately 3.15 inches (8 cm) in length from the top of the second end portion 5 to the bottom of the first end portion 4. The substantially parallel frame portions 27,28 each have four slots 7 in the frame edge 11 remote from the frame aperture 6, with the slots 7 being spaced approximately 0.55 inches (1.4 cm) apart and the slots closest to the second end portion 5 being approximately 0.86 inches (2.18 cm) from the top of the second end portion 5. Preferably, the frame 26 of FIGS. 8 and 9 is formed into frames of three different lordotic curvatures; flat, arc of a circle of 5 inches (13.2 cm) radius and arc of a circle of 7 inches (17.8 cm) radius.

FIGS. 10 to 14 illustrate further alternative embodiments of the present invention.

Figure 12:
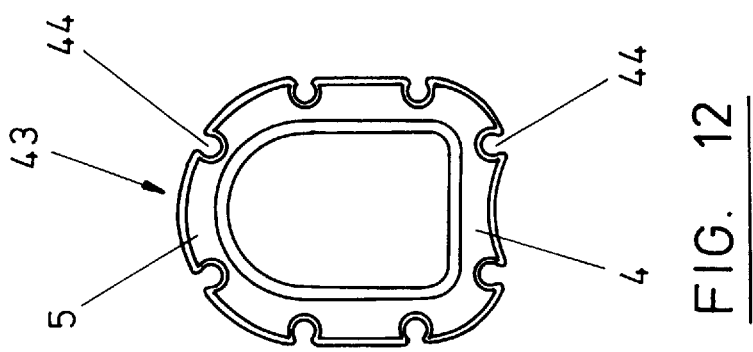
FIGS. 10, 11 and 12 are plan views of further alternative embodiments of the present invention.
Figure 11:
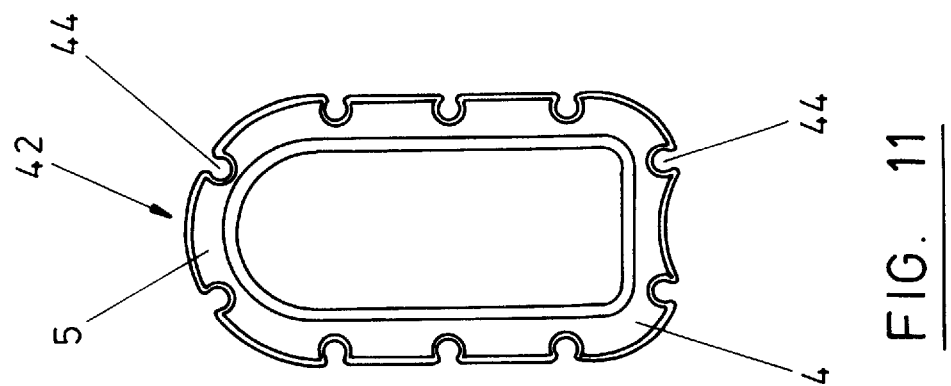
Figure 10:
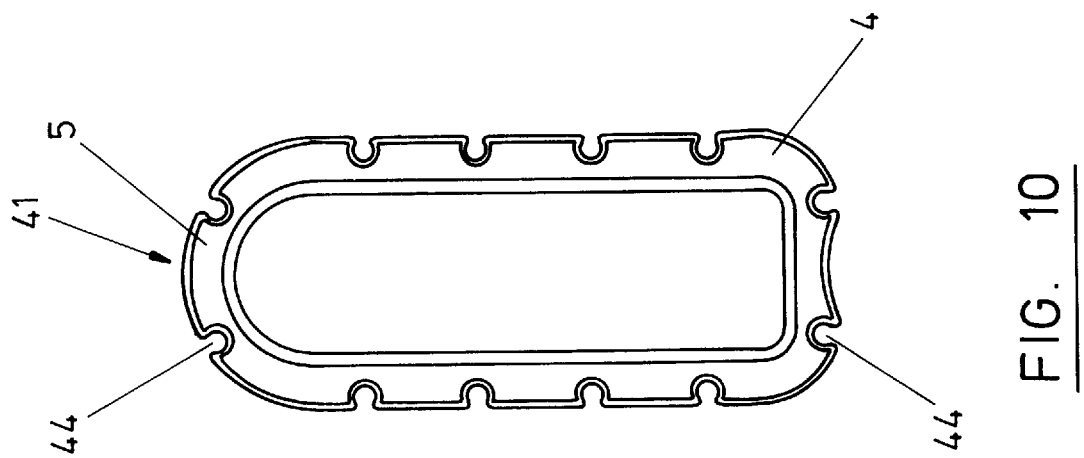

FIGS. 10, 11 and 12 illustrate titanium frames 41,42,43 similar to frames 26,18,1 of FIGS. 8,6 and 1 respectively but having slots 44 in the frame end portions 4,5. The frame end portions 4,5 each have two slots 44 in the frame edge 11 remote from the frame aperture 6 in addition to the slots 7 in the parallel frame portions 2,3. The embodiments of FIGS. 10,11 and 12 do not have grooves in the frame edge 12 adjacent the frame aperture.

Figure 13:
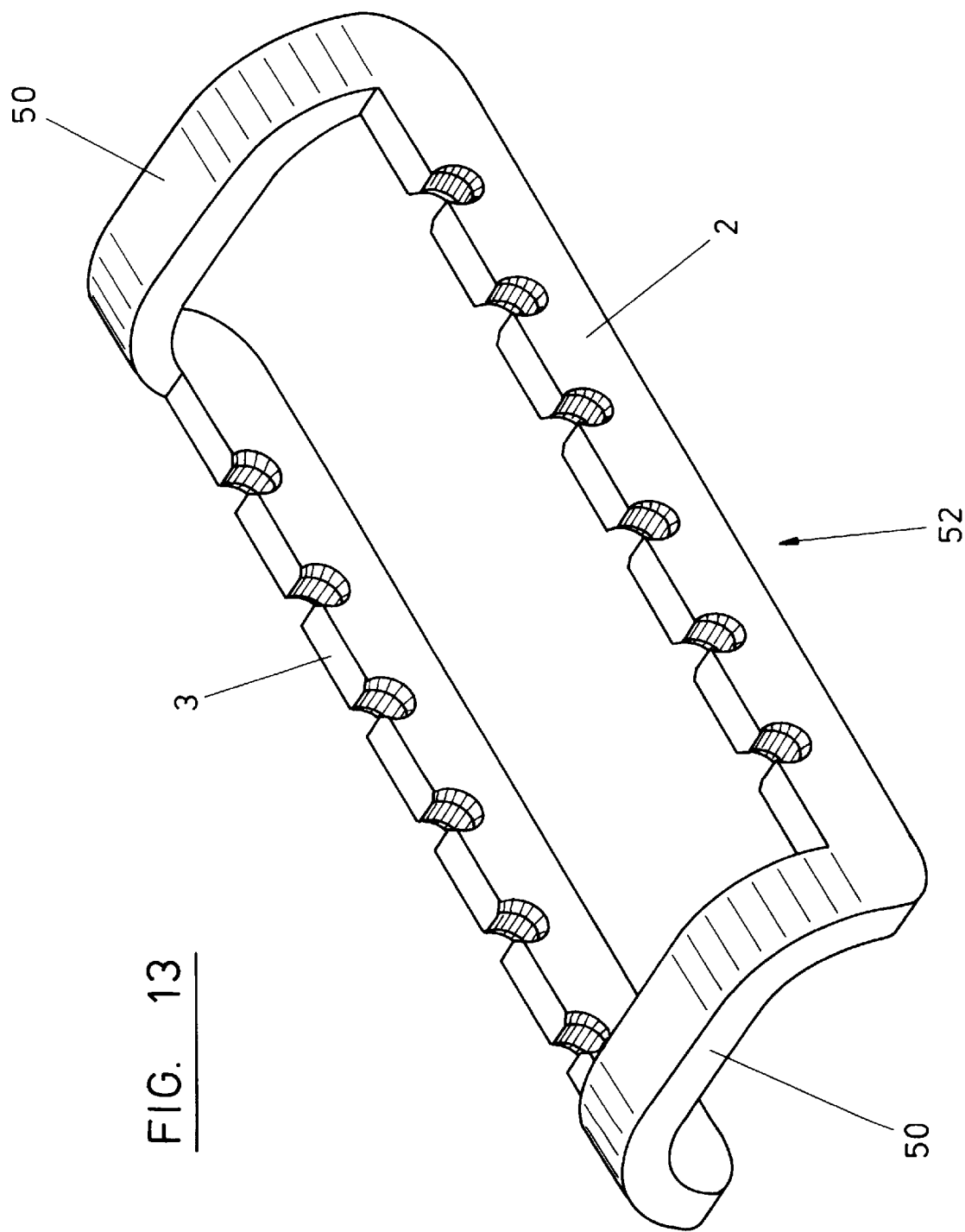
FIGS. 13 and 14 are respective views of further alternative embodiments of the present invention.
Figure 14:
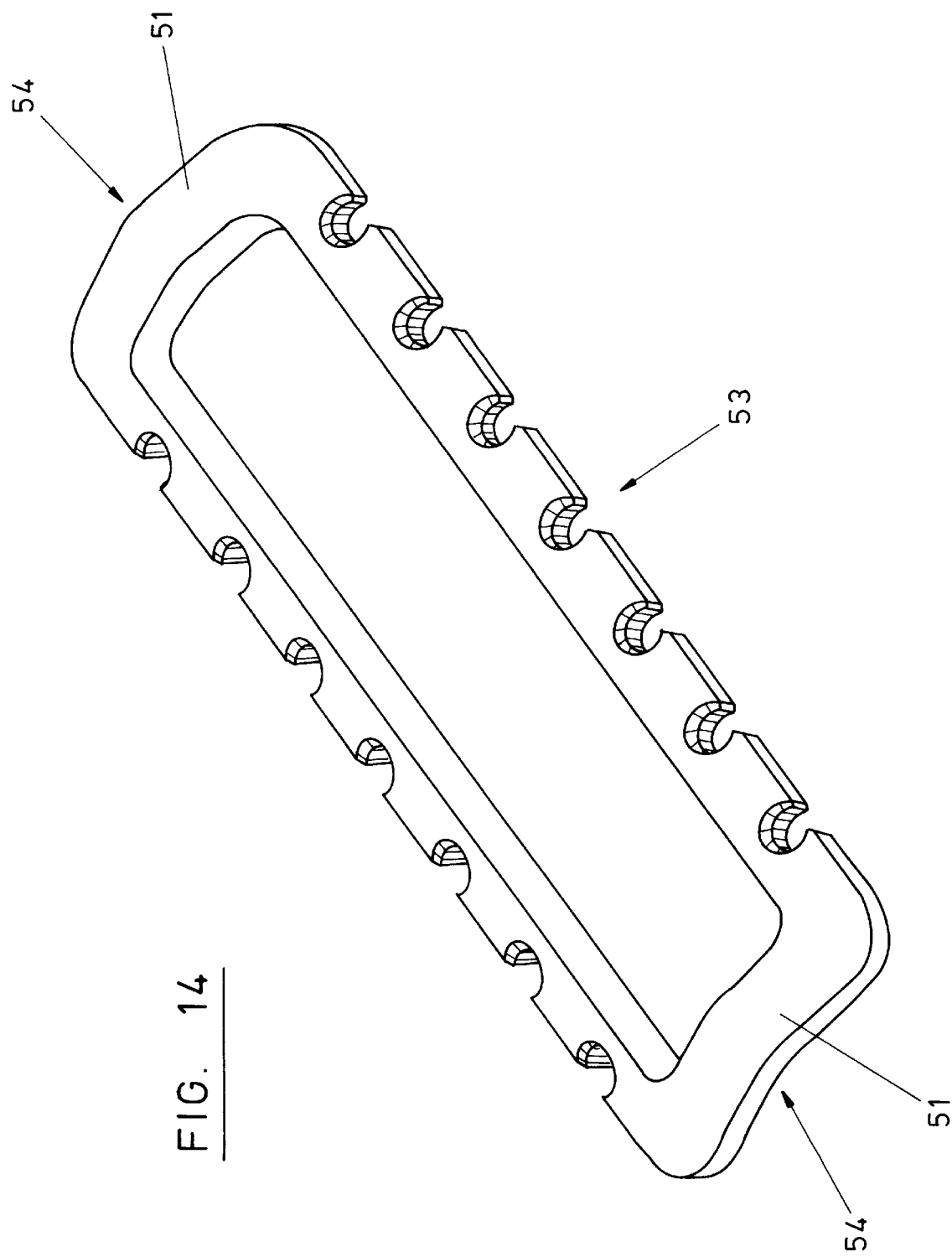

FIGS. 13 and 14 illustrate two alternative types of frame end portion 50,51.

Referring to FIG. 13, a titanium frame 52 is provided with U-shaped frame end portions 50 connecting the parallel frame portions 2,3.

Referring to FIG. 14, a titanium frame 53 is provided with bent end frame portions 51 having a shallow bend 54.

Figures 15, 16:
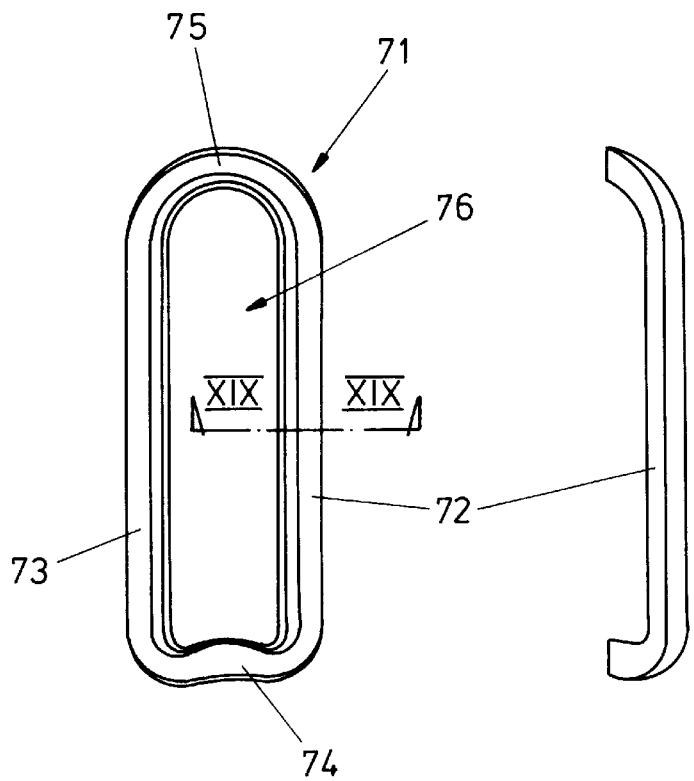
FIG. 15 is a plan view of an alternative embodiment of a surgical implant embodying the present invention.
FIG. 16 is a side view of the surgical implant of FIG. 15.
Figure 19:
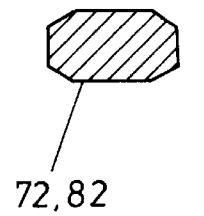
FIG. 19 is a section along line XIX—XIX of FIGS. 15 or 17.

Referring to FIGS. 15 and 16, an alternative titanium alloy frame 71 having first and second substantially parallel frame portions 72,73 respectively, connected by first and second transverse bent (see FIG. 19) shorter end frame portions 74,75 respectively, defines a substantially bullet-shaped aperture 76 (see FIG. 15) for receiving projecting spinal elements.

Figure 21:
FIG. 21 is an end view of the surgical implants of FIG. 15 and 17.
Figure 20:
FIG. 20 is a section similar to that of FIG. 6 through an alternative frame construction.

The frame 71 is formed from titanium alloy (Ti-6Al-4V) sheet stock and has similar dimensions to those of the frames described above. The frame portions have a rectangular cross-section with chamfered corners (see FIG. 20). The frame portions may alternatively be of rectangular cross-section with rounded corners (see FIG. 21).

Referring to FIG. 15, the first frame end portion 74 curves slightly into the aperture (but is otherwise substantially straight) and the second frame end portion is substantially semi-circular (i.e. bent).

Figures 17, 18:
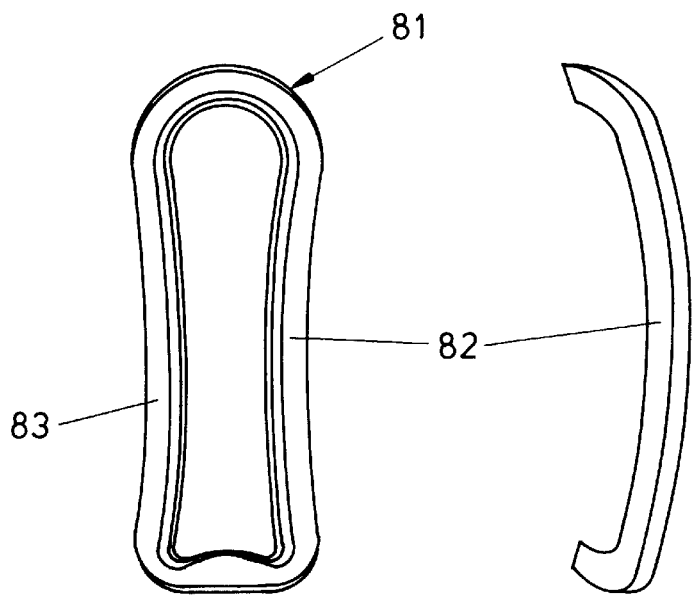
FIG. 17 is a plan view of an alternative embodiment of the present invention.
FIG. 18 is a side view of the surgical implant of FIG. 17.

An alternative construction of a frame similar to that of FIGS. 15 and 16 is shown in FIGS. 17 and 18. The parallel frame portions 82,83 of the frame 81 curve as shown in FIG. 18 so as to accommodate curvature of the spine (i.e. lordosis or kyphosis). In other respects the construction of the frame 81 of FIGS. 17 and 18 is similar to that of the frame 71 of FIGS. 15 and 16.

As discussed above for the frame of FIG. 1 the bullet shaped frames 71,81 have superior conformance to the contours of the spine in comparison to the prior art spinal implants. The "tented" implant with a bullet shaped aperture has been found to fit more closely to the spine and hence reduces the dead space between the spine and the fixed implant.

The bullet shaped frame also leads to greater stability of the fixed implant as a result of an increased contact area between the fixed frame and bone. Using a frame of rectangular cross-section as described above leads to a further increased frame/bone contact area and hence to still greater stability. The generally rectangular cross-section provides more contact with the bony elements of the spine that the traditional prior art circular cross-section.

A frame having the combination of both a bullet shape and with frame portions of rectangular cross-section is the most effective and stable implant construction.

The surgical implants illustrated allow one to rigidly anchor the surgical implant to the spine and prevent relative movement of the implant and fixation wires or cables. It will be appreciated that various modifications may be made for example in the slot distribution and dimensions, without departing from the idea of the present invention.

We claim:

1. A surgical implant for spinal fixation comprising a rigid biocompatible frame defining an aperture, the frame consisting of first and second frame portions substantially parallel to a longitudinal axis of the implant said first and second frame portions being connected by third and fourth frame portions which are shorter then said first and second frame portions, said third and fourth frame portions each bent perpendicular to the longitudinal axis of the implant at least one of said third and fourth frame portions curved away from said aperture so as to define a tapered end portion of the implant which, in use, is adapted to be fitted closely about the spine.

2. A surgical implant according to claim 1, wherein the third frame portion is curved and the fourth frame portion is substantially perpendicular to the first and second frame portions so as to define a substantially bullet-shaped frame aperture.

3. A surgical implant according to claim 1 wherein the frame portions each have a substantially rectangular cross-section.

4. A surgical implant according to claim 3 wherein the first and second frame portions are curved so as to match the curvature of a portion of the spine.

5. A surgical implant according to claim 1 wherein the first and second frame portions are curved so as to match the curvature of a portion of the spine.

6. A surgical implant according to claim 1 wherein the first and second frame portions are substantially straight.

7. A surgical implant for spinal fixation comprising a rigid biocompatible frame defining an aperture, the frame consisting of first and second frame portions substantially parallel to a longitudinal axis of the implant, said first and second frame portions being connected by third and fourth frame portions which are shorter then said first and second frame portions, said third and fourth frame portions each bent perpendicular to the longitudinal axis of the implant the frame having a plurality of recesses formed therein for receiving wire at selected points on the frame and adapted to fix the wire relative thereto.

8. A surgical implant according to claim 7 wherein the frame has at leat one recess opening into the frame aperture.

9. A surgical implant according to claim 7, wherein the frame has an edge remote from the frame aperture, and said edge has at least one recess extending into said edge.

10. A surgical implant according to claim 7 wherein the frame portion each have a substantially rectangular cross section.

11. A surgical implant according to claim 10 wherein the frame portions each have first and second edges, said first edge being contiguous with the frame aperture and said second edge being remote from said frame aperture, wherein said edges of the frame portions are chamfered.

12. A surgical implant according to claim 7 wherein the first and second frame portions are curved so as to match the curvature of a portion of the spine.

13. A surgical implant according to claim 7 wherein the fourth frame portion has first and second ends connected to the first and second frame portions respectively and a middle section between said first and second ends, wherein said fourth frame portion forms a shallow curve with the middle section of the fourth frame portion extending into the frame aperture.

14. A surgical implant according to claim 7 wherein the first and second frame portions are curved so as to match the curvature of a portion of the spine.

15. A surgical implant according to claim 7 wherein the first and second frame portions are substantially straight.

16. A surgical implant according to claim 7 wherein the frame is formed of a titanium alloy.

* * * * *

UNITED STATES PATENT AND TRADEMARK OFFICE
CERTIFICATE OF CORRECTION

PATENT NO. : 5,879,385
DATED : March 9, 1999
INVENTOR(S) : Crockard et al

It is certified that error appears in the above-identified patent and that said Letters Patent is hereby corrected as shown below:

On the title page, item [73]:

Assignee should read --Johnson & Johnson Professional, Inc.--.

Signed and Sealed this

Sixteenth Day of May, 2000

Attest:

Q. TODD DICKINSON

*Attesting Officer*          *Director of Patents and Trademarks*